United States Patent
Thomas, III

(12) 
(10) Patent No.: US 6,453,903 B1
(45) Date of Patent: Sep. 24, 2002

(54) CONDOM WITH CONSTRICTIVE BAND ABOUT OPENING

(76) Inventor: Kirtis Thomas, III, 21924 Frazer, Southfield, MI (US) 48075

( * ) Notice: Subject to any disclaimer, the term of this patent is extended or adjusted under 35 U.S.C. 154(b) by 0 days.

(21) Appl. No.: 09/905,576

(22) Filed: Jul. 13, 2001

(51) Int. Cl.[7] ................................................ A61F 6/04
(52) U.S. Cl. ..................................... 128/844; 128/918
(58) Field of Search ............................. 128/842, 844, 128/918; 604/347–353

(56) References Cited

U.S. PATENT DOCUMENTS 2,586,674 A * 2/1952 Lönne ........................ 128/844
5,361,779 A * 11/1994 Wilson ....................... 128/844
5,513,652 A * 5/1996 Schwartz .................... 128/842
5,622,186 A * 4/1997 Schwartz .................... 128/844

* cited by examiner

*Primary Examiner*—Michael A. Brown
(74) *Attorney, Agent, or Firm*—Harness, Dickey & Pierce, P.L.C.

(57) ABSTRACT

A condom is described having a broad constrictive band adjacent the proximal end in order to maintain the blood supply in the erect penis and thereby maintain and prolong the erection. The proximal constrictive band is molded integral with the latex condom material or formed as a separate band of a rubber material. The separate band may be adhesively attached or solvent welded to the latex condom. Alternatively, the band may be used separate from the condom.

22 Claims, 1 Drawing Sheet

CONDOM WITH CONSTRICTIVE BAND ABOUT OPENING

FIELD OF THE INVENTION

The invention pertains to condoms and, in particular, to condoms for the prevention of the transmission of disease for the temporary assistance in overcoming certain forms of impotence.

BACKGROUND OF THE INVENTION

A variety of condoms and prophylactic devices have been disclosed for the prevention of pregnancy or transmission of disease and for treatment of impotence.

U.S. Pat. No. 2,358,440, the entire specification incorporated herein by reference, discloses a protective finger sheath for medical and surgical use. The open H end of the sheath includes an elastic portion to form a seal about the physician's finger and thereby prevent disease elements and other foreign matter from contacting the finger or the finger from contacting the patient.

U.S. Pat. No. 4,869,723 and U.S. Pat. No. 4,966,166, the entire specifications incorporated herein by reference, disclose condoms with an elastic lesser diameter sealing area adjacent the open end. In the former patent, the elastic portion includes an adhesive applied to the inner surface. In the latter patent, the adhesive band is optional and covered by a peel-away liner before use.

U.S. Pat No. 4,798,600, the entire specification incorporated herein by reference, discloses an elastic band integrally formed about the open end of the condom to act as a seal against the leakage of semen from within the condom.

U.S. Pat. No. 4,964,416, the entire specification incorporated herein by reference, discloses a separate annular sealing element adjacent the open end and a second separate annular sealing element toward the closed end of the condom.

U.S. Pat. No. 4,869,241, the entire specification incorporated herein by reference, discloses a disposable internally applied penile erector that may be used in combination with a condom or external elastic rubber sleeve. In such combination, the device aids in maintaining or prolonging an existing erection by constriction of blood flow.

Although the above patents disclose sealing configurations to prevent the passage of liquids or solids from the open ends of the prophylactic devices, none disclose particular or specific configurations to retain blood within the penis and thereby prolong an erection.

SUMMARY OF THE INVENTION

The present invention generally comprises an improved condom configuration to constrict the penis near the base thereof and to thereby substantially reduce blood flow and therefore prolong or maintain an erection.

The constrictive device preferably comprises a broad constrictive band adjacent the proximal end of the condom to maintain the blood supply within the penis and thereby maintain and prolong the erection. The proximal constrictive band is preferably molded integral with the latex condom material or formed as a separate band of a woven rubber material. The separate band may be adhesively attached or solvent welded to the latex condom. Alternatively, the band may be applied separate from the condom.

In accordance with a first embodiment of the present invention, a condom is provided, comprising: (1) a hollow tubular sheath closed at a distal end thereof and open at a proximal end thereof; and (2) a constrictive band adjacent the proximal open end, said constrictive band having a modulus of elasticity at least one order of magnitude greater than the elasticity of the hollow tubular sheath beyond the constrictive band.

In accordance with a second embodiment of the present invention, a condom is provided, comprising: (1) a hollow tubular sheath closed at a distal end thereof and open at a proximal end thereof; and (2) a constrictive band adjacent the proximal open end, said constrictive band having a modulus of elasticity at least one order of magnitude greater than the elasticity of the hollow tubular sheath beyond the constrictive band; wherein said modulus of elasticity is sufficient to cause constriction of the base of the penis sufficient to substantially reduce blood flow.

In accordance with a third embodiment of the present invention, a condom is provided, comprising: (1) a hollow tubular sheath closed at a distal end thereof and open at a proximal end thereof; and (2) a constrictive band adjacent the proximal open end, said constrictive band having a modulus of elasticity at least one order of magnitude greater than the elasticity of the hollow tubular sheath beyond the constrictive band; wherein said modulus of elasticity is sufficient to cause constriction of the base of the penis sufficient to substantially reduce blood flow; wherein the constrictive band comprises substantially inelastic threads woven into a matrix of elastic threads, said inelastic threads generally extending parallel to the axis of the hollow tubular sheath.

In accordance with a fourth embodiment of the present invention, a condom is provided, comprising: (1) a hollow tubular sheath closed at a distal end thereof and open at a proximal end thereof; and (2) a constrictive band adjacent the proximal open end, said constrictive band having a modulus of elasticity at least one order of magnitude greater than the elasticity of the hollow tubular sheath beyond the constrictive band; wherein said modulus of elasticity is sufficient to cause constriction of the base of the penis sufficient to substantially reduce blood flow; wherein the surface of the constrictive band is corrugated parallel to the axis of the hollow tubular sheath.

A more complete appreciation of the present invention and its scope can be obtained from the following detailed description of the invention and the drawings.

BRIEF DESCRIPTION OF THE DRAWINGS

The present invention will become more fully understood from the detailed description and the accompanying drawings, wherein.

The same reference numerals refer to the same parts throughout the various Figures.

DETAILED DESCRIPTION OF THE INVENTION

Figure 1:
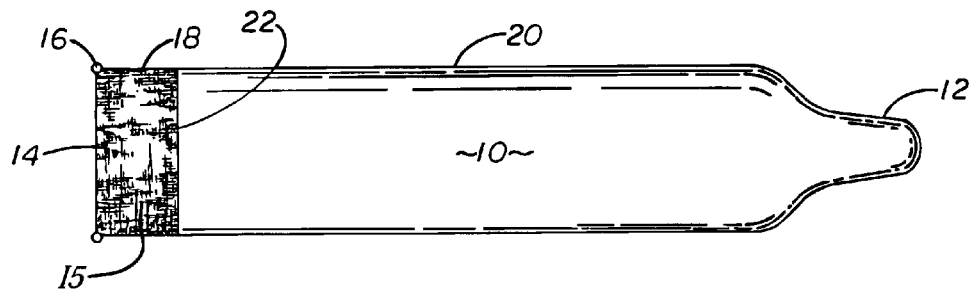
FIG. 1 illustrates a side view of the condom with integral constrictive band.
Figure 2:
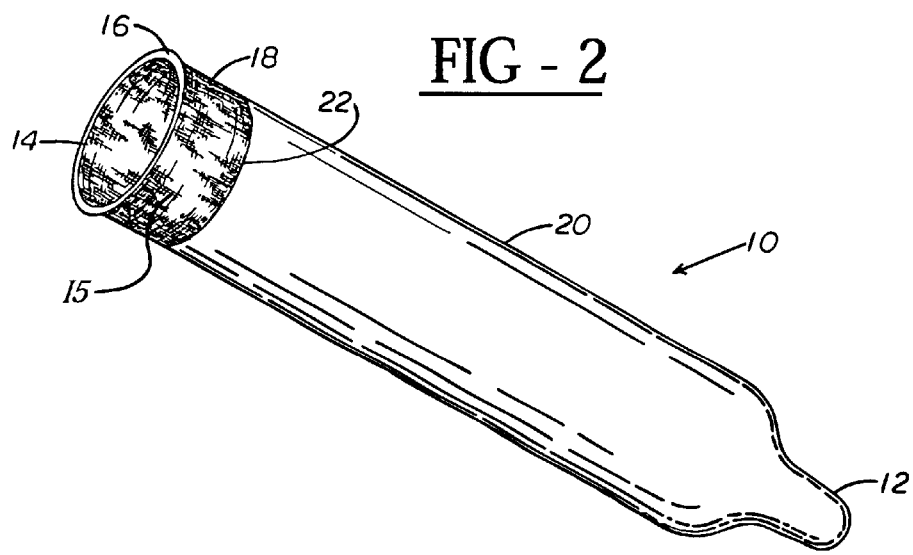
FIG. 2 illustrates a perspective view of the condom with integral constrictive band.

As generally Illustrated in FIGS. 1 and 2, a latex condom 10 is shown having a relatively smaller diameter tip 12 formed at the distal end of the condom 10. The proximal end 14 of the condom 10 is open and circumferentially bordered by a small bead 16 about the opening. Adjacent the proximal end 14 is a constriction band 18 that may be manufactured integral with the hollow tubular sheath 20 of the condom 10.

The constrictive band 18 may be constructed of a corrugated woven rubber and thread material with the thread and corrugations 15 extending parallel to the axis of the sheath 20 and the woven rubber extending circumferentially about the condom 10. A suitable material for the constrictive band 18 is sold under the tradename Medi-Rip® and used as a self-adherent bandage. By way of a no-limiting example, a small tubular strip about three-quarters of an inch long and formed to a one-and-a-half inch diameter is suitable.

To manufacture the integral form of the condom 10, the tubular constrictive band 18 is typically placed on a dipping mandrel toward the proximal end of the mandrel. The proximal end of the mandrel is then dipped momentarily into a latex bath to contact the proximal edge of the constrictive band and form a latex bead 16 around the proximal open end 14 of the condom 10. The mandrel distal end is then dipped into a latex bath to a depth sufficient to contact the latex with the distal circumferential edge 22 of the constrictive band 18. In this manner, the constrictive band 18 is integrally joined to the latex hollow tubular sheath 20.

In placing the constrictive band 18 on a mandrel, the constrictive band 18 is extended or expanded radially, thereby assuring that after the condom 10 is manufactured, the constrictive band 18 will tightly and effectively engage the base of the penis to thereby effectively prevent or retard venous blood flow from the penis before and during intercourse. The tightness of the constrictive band 18, in combination with the integral joining of the constrictive band 18 to the sheath 20 at the distal edge 22 of the band, provides a seal against leakage of fluid into or from within the condom 10 during intercourse.

To be particularly effective, the constrictive band 18 must be significantly less elastic (i.e., possess a significantly greater modulus of elasticity) than the latex of the condom sheath 20. By way of a non-limiting example, at least an order of magnitude difference in elasticity is suitable. The band material, however, must be compatible with the latex for ease of manufacture and assurance that the bond between the constrictive band 18 and sheath 20 will not fail in storage or in intercourse. Although described in terms of woven rubber and latex because latex condoms are currently considered most effective, other materials, particularly synthetic materials such as urethane rubbers, might also be suitable.

Figure 3:
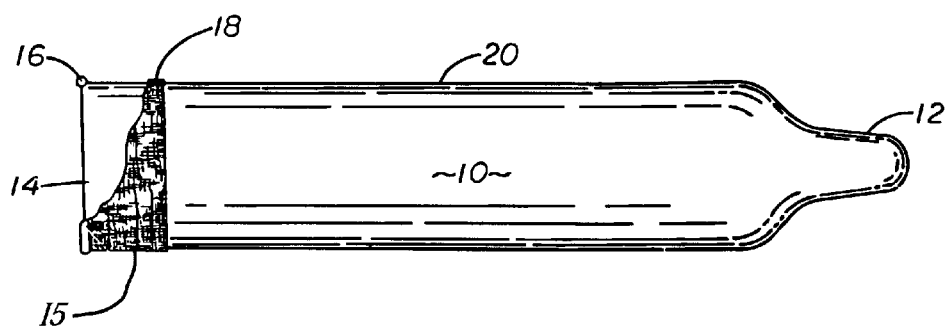
FIG. 3 illustrates a side broken away cross-section view of an alternative construction of the condom with a separate constrictive band.

As an alternative as shown generally in FIG. 3, the constrictive band 18 may be placed on the outside of a previously manufactured condom 10 and solvent welded or adhesively affixed to the sheath 20 to retain the constrictive band 18 adjacent the proximal end 14 and bead 16. In manufacture, the constrictive band 18 may be stretched and placed over the sheath 20 before the condom 10 is removed from the dipping mandrel.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention.

What is claimed is:

1. A condom, comprising:
    a hollow tubular sheath closed at a distal end thereof and open at a proximal end thereof; and
    a constrictive band adjacent the proximal open end, said constrictive band having a modulus of elasticity at least one order of magnitude greater than the elasticity of the hollow tubular sheath beyond the constrictive band.

2. The invention as recited in claim 1, wherein the constrictive band is formed integral with the hollow tubular sheath.

3. The invention as recited in claim 1, wherein the constrictive band is solvent welded to the hollow tubular sheath.

4. The invention as recited in claim 1, wherein the constrictive band is adhesively affixed to the hollow tubular sheath.

5. The invention as recited in claim 1, wherein the constrictive band comprises substantially inelastic threads woven into a matrix of elastic threads, said inelastic threads generally extending parallel to the axis of the hollow tubular sheath.

6. The invention as recited in claim 1, wherein the surface the constrictive band is corrugated parallel to the axis of the hollow tubular sheath.

7. A condom, comprising:
    a hollow tubular sheath closed at a distal end thereof and open at a proximal end thereof; and
    a constrictive band adjacent the proximal open end, said constrictive band having a modulus of elasticity at least one order of magnitude greater than the elasticity of the hollow tubular sheath beyond the constrictive band;
    wherein said modulus of elasticity is sufficient to cause constriction of the base of the penis sufficient to substantially reduce blood flow.

8. The invention as recited in claim 7, wherein the constrictive band is formed integral with the hollow tubular sheath.

9. The invention as recited in claim 7, wherein the constrictive band is solvent welded to the hollow tubular sheath.

10. The invention as recited in claim 7, wherein the constrictive band is adhesively affixed to the hollow tubular sheath.

11. The invention as recited in claim 7, wherein the constrictive band comprises substantially inelastic threads woven into a matrix of elastic threads, said inelastic threads generally extending parallel to the axis of the hollow tubular sheath.

12. The invention as recited in claim 7, wherein the surface of the constrictive band is corrugated parallel to the axis of the hollow tubular sheath.

13. A condom, comprising:
    a hollow tubular sheath closed at a distal end thereof and open at a proximal end thereof; and
    a constrictive band adjacent the proximal open end, said constrictive band having a modulus of elasticity at least one order of magnitude greater than the elasticity of the hollow tubular sheath beyond the constrictive band;
    wherein said modulus of elasticity is sufficient to cause constriction of the base of the penis sufficient to substantially reduce blood flow;
    wherein the constrictive band comprises substantially inelastic threads woven into a matrix of elastic threads, said inelastic threads generally extending parallel to the axis of the hollow tubular sheath.

14. The invention as recited in claim 13, wherein the constrictive band is formed integral with the hollow tubular sheath.

15. The invention as recited in claim 13, wherein the constrictive band is solvent welded to the hollow tubular sheath.

16. The invention as recited in claim 13, wherein the constrictive band is adhesively affixed to the hollow tubular sheath.

17. The invention as recited in claim 13, wherein the surface of the constrictive band is corrugated parallel to the axis of the hollow tubular sheath.

18. A condom, comprising:
- a hollow tubular sheath closed at a distal end thereof and open at a proximal end thereof; and
- a constrictive band adjacent the proximal open end, said constrictive band having a modulus of elasticity at least one order of magnitude greater than the elasticity of the hollow tubular sheath beyond the constrictive band;
- wherein said modulus of elasticity is sufficient to cause constriction of the base of the penis sufficient to substantially reduce blood flow;
- wherein the surface of the constrictive band is corrugated parallel to the axis of the hollow tubular sheath.

19. The invention as recited in claim 18, wherein the constrictive band comprises substantially inelastic threads woven into a matrix of elastic threads, said inelastic threads generally extending parallel to the axis of the hollow tubular sheath.

20. The invention as recited in claim 18, wherein the constrictive band is formed integral with the hollow tubular sheath.

21. The invention as recited in claim 18, wherein the constrictive band is solvent welded to the hollow tubular sheath.

22. The invention as recited in claim 18, wherein the constrictive band is adhesively affixed to the hollow tubular sheath.

* * * * *

UNITED STATES PATENT AND TRADEMARK OFFICE
CERTIFICATE OF CORRECTION

PATENT NO. : 6,453,903 B1 Page 1 of 1
APPLICATION NO. : 09/905576
DATED : September 24, 2002
INVENTOR(S) : Kirtis Thomas, III It is certified that error appears in the above-identified patent and that said Letters Patent is hereby corrected as shown below:

Column 1, line 17, after "open" delete "H".

Column 2, line 65, "Illustrated" should be --illustrated--.

Column 3, line 11, "no-limiting" should be --non-limiting--.

Column 4, line 16, Claim 6, after "surface" insert --of--.

Signed and Sealed this

Tenth Day of July, 2007

JON W. DUDAS
*Director of the United States Patent and Trademark Office*